(12) United States Patent
Ralston et al.

(10) Patent No.: US 6,274,148 B1
(45) Date of Patent: *Aug. 14, 2001

(54) HEPATITIS C VIRUS ASIALOGLYCOPROTEINS

(75) Inventors: Robert O. Ralston; Frank Marcus, both of Danville; Kent B. Thudium, Oakland; Barbara A. Gervase, Vallejo; John A. Hall, Rohnert Park; Kim M. Berger, Lafayette; Qui-Lim Choo, El Cerrito; Michael Houghton, Danville; George Kuo, San Francisco, all of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/249,843

(22) Filed: May 26, 1994

Related U.S. Application Data

(63) Continuation-in-part of application No. 07/758,880, filed on Sep. 13, 1991, now abandoned, which is a continuation-in-part of application No. 07/611,419, filed on Nov. 8, 1990, now abandoned.

(51) Int. Cl.[7] .............................. A61K 39/29; C12Q 1/70
(52) U.S. Cl. ................... 424/228.1; 424/185.1; 424/204.1; 435/5; 435/69.3; 435/69.9; 530/350; 530/395; 530/826
(58) Field of Search .................. 435/5, 69.9, 69.3; 424/185.1, 204.1, 228.1; 530/395, 350, 826

(56) References Cited

U.S. PATENT DOCUMENTS

| | | | |
|---|---|---|---|
| 5,135,854 | * 8/1992 | MacKay et al. | 435/69.1 |
| 5,350,671 | * 9/1994 | Houghton et al. | 435/5 |

FOREIGN PATENT DOCUMENTS

| | | |
|---|---|---|
| 0 318 216 A1 | 5/1989 | (EP) . |
| 0 320 267 | 6/1989 | (EP) . |
| 0 388 232 A1 | 9/1990 | (EP) . |
| WO 91/15771 | 10/1991 | (WO) . |
| 92/08734 | 5/1992 | (WO) . |

OTHER PUBLICATIONS

Lanford et al., "Analysis of Hepatitis C Virus Capsid, E1, and E2/NS1 Proteins Expressed in Insect Cells," *Virology* 197:225–235 (1993).
Spaete et al., "Characterization of the Hepatitis C Virus E2/NS1 Gene Product Expressed in Mammalian Cells," *Virology* 188:819–830 (1992).
Kukuruzinska et al. Ann. Rev. Biochem 1987 56:915–944 "Protein Glycosylation in Yeast".*
Hijikata et al., "Gene Mapping of the Putative. . . ," Proc. Natl. Acad. Sci 88:5547–51 (1991).*
Hodo, "Lectins as Tools for the Purification of Membrane Receptors," *Receptor Purification Procedures* (Alan R. Liss, NY) pp 45–60 (1984).*
Goochee et al, "The oligosaccharides of glycoproteins. . . ," Biotechnology 9:1347–1355(1991).*
Saunders Dictionary & Encyclopedia of Laboratory Medicine and Technology, p 138 (1987).*

* cited by examiner

*Primary Examiner*—Marianne P. Allen
*Assistant Examiner*—Mary K. Zeman
(74) *Attorney, Agent, or Firm*—Roberta L. Robins; Alisa A. Harbin; Robert P. Blackburn

(57) ABSTRACT

Two Hepatitis C Virus envelope proteins (E1 and E2) are expressed without sialylation. Recombinant expression of these proteins in lower eukaryotes, or in mammalian cells in which terminal glycosylation is blocked, results in recombinant proteins which are more similar to native HCV glycoproteins. When isolated by GNA lectin affinity, the E1 and E2 proteins aggregate into virus-like particles.

25 Claims, No Drawings

HEPATITIS C VIRUS ASIALOGLYCOPROTEINS

RELATED APPLICATIONS

This application is a continuation-in-part of U.S. Ser. No. 07/758,880, filed Sep. 13, 1991, now abandoned which is a continuation-in-part of U.S. Ser. No. 07/611,419, filed Nov. 8, 1990, now abandoned, the discosures of which are incorporated herein by reference.

DESCRIPTION

1. Technical Field

This invention relates to the general fields of recombinant protein expression and virology. More particularly, the invention relates to glycoproteins useful for diagnosis, treatment, and prophylaxis of Hepatitis C virus (HCV) infection, and methods for producing such glycoproteins.

2. Background of the Invention

Non-A, Non-B hepatitis (NANBH) is a transmissible disease (or family of diseases) that is believed to be virally induced, and is distinguishable from other forms of virus-associated liver disease, such as those caused by hepatitis A virus (HAV), hepatitis B virus (HBV), delta hepatitis virus (HDV), cytomegalovirus (CMV) or Epstein-Barr virus (EBV). Epidemiologic evidence suggests that there may be three types of NANBH: the water-borne epidemic type; the blood or needle associated type; and the sporadically occurring community acquired type. The number of causative agents is unknown. However, a new viral species, hepatitis C virus (HCV) has recently been identified as the primary (if not only) cause of blood-borne NANBH (BB-NANBH). See for example PCT WO89/046699 and U.S. patent application Ser. No. 07/355,002, filed May 18, 1989 now abandoned. Hepatitis C appears to be the major form of transfusion-associated hepatitis in a number of countries or regions, including the United States, Europe, and Japan. There is also evidence implicating HCV in induction of hepatocellular carcinoma. Thus, a need exists for an effective method for preventing and treating HCV infection.

The demand for sensitive, specific methods for screening and identifying carriers of HCV and HCV-contaminated blood or blood products is significant. Post-trans-fusion hepatitis (PTH) occurs in approximately 10% of transfused patients, and HCV accounts for up to 90% of these cases. The major problem in this disease is the frequent progression to chronic liver damage (25–55%).

Patient care, as well as the prevention of transmission of HCV by blood and blood products or by close personal contact, requires reliable diagnostic and prognostic tools to detect nucleic acids, antigens and antibodies related to HCV. In addition, there is also a need for effective vaccines and immunotherapeutic therapeutic agents for the prevention and/or treatment of the disease.

HCV appears in the blood of infected individuals at very low rates relative to other infectious viruses, which makes the virus very difficult to detect. The low viral burden is probably the primary reason that the causative agent of NANB hepatitis went so long undetected. Even though it has now been cloned, HCV still proves difficult to culture and propagate. Accordingly, there is a strong need for recombinant means of producing diagnostic/therapeutic/prophylactic HCV proteins.

DISCLOSURE OF THE INVENTION

It has been found that two HCV proteins, E1 and E2, appear to be membrane associated asialoglycoproteins when expressed in recombinant systems. This is surprising because glycoproteins do not usually remain in mannose-terminated form in mammals, but are further modified with other carbohydrates: the mannose-terminated form is typically only transient. In the case of E1 and E2 (as expressed in our systems), the asialoglycoprotein appears to be the final form. E1 (envelope protein 1) is a glycoprotein having a molecular weight of about 35 kD which is translated from the predicted E1 region of the HCV genome. E2 (envelope protein 2) is a glycoprotein having a molecular weight of about 72 kD which is translated from the predicted NS1 (non-structural protein 1) region of the HCV genome, based on the flaviviral model of HCV. As viral glycoproteins are often highly immunogenic, E1 and E2 are prime candidates for use in immunoassays and therapeutic/prophylactic vaccines.

The discovery that E1 and E2 are not sialylated is significant. The particular form of a protein often dictates which cells may serve as suitable hosts for recombinant expression. Prokaryotes such as $E.$ $coli$ do not glycosylate proteins, and are generally not suitable for production of glycoproteins for use as antigens because glycosylation is often important for full antigenicity, solubility, and stability of the protein. Lower eukaryotes such as yeast and fungi glycosylate proteins, but are generally unable to add terminal sialic acid residues to the carbohydrate complexes. Thus, yeast-derived proteins may be antigenically distinct from their natural (non-recombinant) counterparts. Expression in mammalian cells is preferred for applications in which the antigenicity of the product is important, as the glycosylation of the recombinant protein should closely resemble that of the wild viral proteins.

New evidence indicates that the HCV virus may gain entry to host cells during infection through either the asialoglycoprotein receptor found on hepatocytes, or through the mannose receptor found on hepatic endothelial cells and macrophages (particularly Kupffer cells). Surprisingly, it has been found that the bulk of natural E1 and E2 do not contain terminal sialic acid residues, but are only core-glycosylated. A small fraction additionally contains terminal N-acetylglucosamine. Accordingly, it is an object of the present invention to provide HCV envelope glycoproteins lacking all or substantially all terminal sialic acid residues.

Another aspect of the invention is a method for producing asialo-E1 or E2, under conditions inhibiting addition of terminal sialic acid, e.g., by expression in yeast or by expression in mammalian cells using antibiotics to facilitate secretion or release.

Another aspect of the invention is a method for purifying E1 or E2 by affinity to lectins which bind terminal mannose residues or terminal N-acetylglucosamine residues.

Another aspect of the invention is an immunogenic composition comprising a recombinant asialoglycoprotein selected from the group consisting of HCV E1 and E2 in combination with a pharmaceutically acceptable vehicle. One may optionally include an immunological adjuvant, if desired.

Another aspect of the invention is an immunoassay reagent, comprising a recombinant asialoglycoprotein selected from the group consisting of HCV E1 and E2 in combination with a suitable support. Another immunoassay reagent of the invention comprises a recombinant asialoglycoprotein selected from the group consisting of HCV E1 and E2 in combination with a suitable detectable label.

Another aspect of the invention concerns dimers and higher-order aggregates of E1 and/or E2. One species of the invention is an E2 complex. Another species of the invention is an E1:E2 heterodimer.

Another aspect of the invention is an HCV vaccine composition comprising E1:E2 aggregates and a pharmaceutically acceptable carrier.

Another aspect of the invention is a method for purifying E1:E2 complexes.

MODES OF CARRYING OUT THE INVENTION

A. DEFINITIONS

The term "asialoglycoprotein" refers to a glycosylated protein which is substantially free of sialic acid moieties. Asialoglycoproteins may be prepared recombinantly, or by purification from cell culture or natural sources. Presently preferred asialoglycoproteins are derived from HCV, preferably the glycoproteins E1 and E2, most preferably recombinant E1 and E2 (rE1 and rE2). A protein is "substantially free" of sialic acid within the scope of this definition if the amount of sialic acid residues does not substantially interfere with binding of the glycoprotein to mannose-binding proteins such as GNA. This degree of sialylation will generally be obtained where less than about 40% of the total N-linked carbohydrate is sialic acid, more preferably less than about 30%, more preferably less than about 20%, more preferably less than about 10%, more preferably less than about 5%, and most preferably less than about 2%.

The term "E1" as used herein refers to a protein or polypeptide expressed within the first 400 amino acids of an HCV polyprotein, sometimes referred to as the E or S protein. In its natural form it is a 35 kD glycoprotein which is found strongly membrane-associated. In most natural HCV strains, the E1 protein is encoded in the viral polyprotein following the C (core) protein. The E1 protein extends from approximately amino acid 192 to about aa383 of the full-length polyprotein. The term "E1" as used herein also includes analogs and truncated mutants which are immunologically crossreactive with natural E1.

The term "E2" as used herein refers to a protein or polypeptide expressed within the first 900 amino acids of an HCV polyprotein, sometimes referred to as the NS1 protein. In its natural form it is a 72 kD glycoprotein which is found strongly membrane-associated. In most natural HCV strains, the E2 protein follows the E1 protein. The E2 protein extends from approximately aa384 to about aa820. The term "E2" as used herein also includes analogs and truncated mutants which are immunologically crossreactive with natural E2.

The term "aggregate" as used herein refers to a complex of E1 and/or E 2 containing more than one E1 or E2 monomer. E1:E1 dimers, E2: E2 dimers, and E1:E2 heterodimers are all "aggregates" within the scope of this definition. Compositions of the invention may also include larger aggregates, and may have molecular weights in excess of 800 kD.

The term "particle" as used herein refers to an E1 , E2, or E1/E2 aggregate visible by electron microscopy and having a dimension of at least 20 nm. Preferred particles are those having a roughly spherical appearance and a diameter of approximately 40 mn by electron microscopy.

The term "purified" as applied to proteins herein refers to a composition wherein the desired protein comprises at least 35% of the total protein component in the composition. The desired protein preferably comprises at least 40%, more preferably at least about 50%, more preferably at least about 60%, still more preferably at least about 70%, even more preferably at least about 80%, even more preferably at least about 90%, and most preferably at least about 95% of the total protein component. The composition may contain other compounds such as carbohydrates, salts, lipids, solvents, and the like, without affecting the determination of percentage purity as used herein. An "isolated" HCV asialoglycoprotein intends an HCV asialoglycoprotein composition which is at least 35% pure. "Mannose-binding protein" as used herein intends a lectin or other protein which specifically binds to proteins having mannose-terminated glycosylation (e.g., asialo-glycoproteins), for example, mannose-binding lectins, antibodies specific for mannose-terminated glycosylation, mannose receptor protein (R. A. B. Ezekowitz et al., *J Exp Med* (1990) 176:1785–94), asialoglycoprotein receptor proteins (H. Kurata et al., *J Biol Chem* (1990) 265:11295–98), serum mannose-binding protein (I. Schuffenecker et al., *Cytogenet Cell Genet* (1991) 56:99–102; K. Sastry et al., *J Immunol* (1991) 147:692–97), serum asialoglycoprotein-binding protein, and the like. Mannose-binding lectins include, for example, GNA, Concanavalin A (ConA), and other lectins with similar binding properties.

The term "GNA lectin" refers to *Galanthus nivalus* agglutinin, a commercially available lectin which binds to mannose-terminated glycoproteins.

A "recombinant" glycoprotein as used herein is a glycoprotein expressed from a recombinant polynucleotide, in which the structural gene encoding the glycoprotein is expressed under the control of regulatory sequences not naturally adjacent to the structural gene, or in which the structural gene is modified. For example, one may form a vector in which the E1 structural gene is placed under control of a functional fragment of the yeast glyceraldehyde-3-phosphate dehydrogenase (GAPDH) promoter. A presently preferred promoter for use in yeast is the hybrid ADH2/GAP promoter described in U.S. Pat. No. 4,880,734 (incorporated herein by reference), which employs a fragment of the GAPDH promoter in combination with the upstream activation sequence derived from alcohol dehydrogenase 2. Modifications of the structural gene may include substitution of different codons with degenerate codons (e.g., to utilize host-preferred codons, eliminate or generate restriction enzyme cleavage sites, to control hairpin formation, etc.), and substitution, insertion or deletion of a limited number of codons encoding different amino acids (preferably no more than about 10%, more preferably less than about 5% by number of the natural amino acid sequence should be altered), and the like. Similarly, a "recombinant" receptor refers to a receptor protein expressed from a recombinant polynucleotide, in which the structural gene encoding the receptor is expressed under the control of regulatory sequences not naturally adjacent to the structural gene, or in which the structural gene is modified.

The term "isolated polypeptide" refers to a polypeptide which is substantially free of other HCV viral components, particularly polynucleotides. A polypeptide composition is "substantially free" of another component if the weight of the polypeptide in the composition is at least 70% of the weight of the polypeptide and other component combined, more preferably at least about 80%, still more preferably about 90%, and most preferably 95% or greater. For example, a composition containing 100 µg/ml E1 and only 3 µg/ml other HCV components (e.g., DNA, lipids, etc.) is substantially free of "other HCV viral components", and thus is a composition of an isolated polypeptide within the scope of this definition.

The term "secretion leader" refers to a polypeptide which, when encoded at the N-terminus of a protein, causes the protein to be secreted into the host cell's culture medium following translation. The secretion leader will generally be derived from the host cell employed. For example, suitable secretion leaders for use in yeast include the *Saccharomyces cerevisiae* α-factor leader (see U.S. Pat. No. 4,870,008, incorporated herein by reference).

The term "lower eukaryote" refers to host cells such as yeast, fungi, and the like. Lower eukaryotes are generally (but not necessarily) unicellular. Preferred lower eukaryotes are yeasts, particularly species within Saccharomyces, Schizosaccharomyces, Kluveromyces, Pichia, Hansenula, and the like. *Saccharomyces cerevisiae, S. carlsbergensis* and *K. lactis* are the most commonly used yeast hosts, and are convenient fungal hosts.

The term "higher eukaryote" refers to host cells derived from higher animals, such as mammals, reptiles, insects, and the like. Presently preferred higher eukaryote host cells are derived from Chinese hamster (e.g., CHO), monkey (e.g., COS cells), human, and insect (e.g., *Spodoptera frugiperda*). The host cells may be provided in suspension or flask cultures, tissue cultures, organ cultures, and the like.

The term "calcium modulator" refers to a compound capable of sequestering or binding calcium ions within the endoplasmic reticulum, or affects calcium ion concentration within the ER by its effect on calcium regulatory proteins (e.g., calcium channel proteins, calcium pumps, etc.). Suitable calcium modulators include, for example thapsigargin, EGTA (ethylene glycol bis[β-aminoethyl ether] N,N,N',N'-tetraacetic acid). The presently preferred modulator is thapsigargin (see e.g., O. Thastrup et al, *Proc Nat Acad Sci USA* (1990) 87:2466–70).

The term "immunogenic" refers to the ability of a substance to cause a humoral and/or cellular immune response, whether alone or when linked to a carrier, in the presence or absence of an adjuvant. "Neutralization" refers to an immune response that blocks the infectivity, either partially or fully, of an infectious agent. A "vaccine" is an immunogenic composition capable of eliciting protection against HCV, whether partial or complete, useful for treatment of an individual.

The term "biological liquid" refers to a fluid obtained from an organism, such as serum, plasma, saliva, gastric secretions, mucus, and the like. In general, a biological liquid will be screened for the presence of HCV particles. Some biological fluids are used as a source of other products, such as clotting factors (e.g., Factor VII:C), serum albumin, growth hormone, and the like. In such cases, it is important that the source biological fluid be free of contamination by virus such as HCV.

B. GENERAL METHOD

The E1 region of the HCV genome is described in EP 388,232 as region "E", while E2 is described as "NS 1." The E1 region comprises approximately amino acids 192–383 in the full-length viral polyprotein. The E2 region comprises approximately amino acids 384–820. The complete sequences of prototypes of these proteins (strain HCV-1) are available in the art (see EP 388,232), as are general methods for cloning and expressing the proteins. Both E1 and E2 may be expressed from a polynucleotide encoding the first 850–900 amino acids of the HCV polyprotein (see, e.g., SEQ ID NO:3): post-translational processing in most eukaryotic host cells cleaves the initial polyprotein into C, E1, and E2. One may truncate the 5' end of the coding region to reduce the amount of C protein produced.

Expression of asialoglycoproteins may be achieved by a number of methods. For example, one may obtain expression in lower eukaryotes (such as yeast) which do not normally add sialic acid residues to glycosylated proteins. In yeast expression systems, it is presently preferred to employ a secretion leader such as the *S. cerevisiae* α-factor leader, so that the protein is expressed into the culture medium following translation. It is also presently preferred to employ glycosylation-deficient mutants such as pmr1, as these mutants supply only core glycosylation, and often secrete heterologous proteins with higher efficiency (H. K. Rudolph et al, *Cell* (1989) 58: 133–45). Alternatively, one may employ other species of yeast, such as *Pichia pastotis*, which express glycoproteins containing 8–9 mannose residues in a pattern believed to resemble the core glycosylation pattern observed in mammals and *S. cerevisiae*.

Alternatively, one may arrange expression in mammalian cells, and block terminal glycosylation (addition of sialic acid). Recombinant constructs will preferably include a secretion signal to insure that the protein is directed toward the endoplasmic reticulum. Transport to the golgi appears to be blocked by E1 and E2 themselves: highlevel expression of E1 or E2 in mammalian cells appears to arrest secretion of all cellular proteins at the endoplasmic reticulum or cis golgi. One may additionally employ a glycosylation defective mutant. See for example, P. Stanley, *Ann Rev Genet* (1984) 18:525–52. In the event a glycosylation or transport mutant expresses E1 or E2 with sialylation, the terminal sialic acid residues may be removed by treatment with neuraminidase.

Yield should be further increased by use of a calcium modulator to obtain release of protein from within the endoplasmic reticulum. Suitable modulators include thapsigargin, EGTA, and A23817 (see e.g., O. Thastrup et al, *Proc Nat Acad Sci USA* (1990) 87:2466–70). For example, one may express a large amount of E1 or E2 intracellularly in mammalian cells (e.g., CHO, COS, HeLa cells, and the like) by transfection with a recombinant vaccinia virus vector. After allowing time for protein expression and accumulation in the endoplasmic reticulum, the cells are exposed to a calcium modulator in concentration large enough to cause release of the ER contents. The protein is then recovered from the culture medium, which is replaced for the next cycle.

Additionally, it may be advantageous to express a truncated form of the envelope protein. Both E1 and E2 appear to have a highly hydrophobic domain, which apparently anchors the protein within the endoplasmic reticulum and prevents efficient release. Thus, one may wish to delete portions of the sequence found in one or more of the regions aa1170–190, aa260–290 or aa330–380 of E1 (numbering from the beginning of the polyprotein), and aa660–830 of E2 (see for example FIG. 20-1 of EP 388,232). It is likely that at least one of these hydrophobic domains forms a transmembrane region which is not essential for antigenicity of the protein, and which may thus be deleted without detrimental effect. The best region to delete may be determined by conducting a small number of deletion experiments within the skill of the ordinary practitioner. Deletion of the hydrophobic 3' end of E2 results in secretion of a portion of the E2 expressed, with sialylation of the secreted protein.

One may use any of a variety of vectors to obtain expression. Lower eukaryotes such as yeast are typically transformed with plasmids using the calcium phosphate precipitation method, or are transfected with a recombinant virus. The vectors may replicate within the host cell independently, or may integrate into the host cell genome. Higher eukaryotes may be transformed with plasmids, but are typically infected with a recombinant virus, for example a recombinant vaccinia virus. Vaccinia is particularly preferred, as infection with vaccinia halts expression of host cell proteins. Presently preferred host cells include HeLa and plasmacytoma cell lines. In the present system, this means that E1 and E2 accumulate as the major glycosylated species in the host ER. As the rE1 and rE2 will be the predominant glycoproteins which are mannose-terminated, they may easily be purified from the cells by using lectins such as *Galanthus nivalus* agglutinin (GNA) which bind terminal mannose residues.

Proteins which are naturally expressed as mannose-terminated glycoproteins are relatively rare in mammalian physiology. In most cases, a mammalian glycoprotein is mannose-terminated only as a transient intermediate in the glycosylation pathway. The fact that HCV envelope proteins, expressed recombinantly, contain mannose-tenninated glycosylation or (to a lesser degree) N-acetylglucosamine means that HCV proteins and whole virions may be separated and partially purified from endogenous proteins using lectins specific for terminal mannose or N-acetylglucosamine. The recombinant proteins appear authentic, and are believed essentially identical to the envelope proteins found in the mature, free virion, or to a form of cell-associated envelope protein. Thus, one may employ lectins such as GNA for mannose-terminated proteins, and WGA (wheat germ agglutinin) and its equivalents for N-acetylglucosamine-terminated proteins. One may employ lectins bound to a solid phase (e.g., a lectin-Sepharose® column) to separate E1 and E2 from cell culture supernatants and other fluids, e.g., for purification during the production of antigens for vaccine or immunoassay use.

Alternatively, one may provide a suitable lectin to isolate E1, E2, or HCV virions from fluid or tissue samples from subjects suspected of HCV infection. As man-nose-terminated glycoproteins are relatively rare, such a procedure should serve to purify the proteins present in a sample, substantially reducing the background. Following binding to lectin, the HCV protein may be detected using anti-HCV antibodies. If whole virions are present, one may alternatively detect HCV nucleic acids using PCR techniques or other nucleic acid amplification methods directed toward conserved regions of the HCV genome (for example, the 5' non-coding region). This method permits isolation and characterization of differing strains of HCV without regard for antigenic drift or variation, e.g., in cases where a new strain is not immunologically crossreactive with the strain used for preparing antibodies. There are many other ways to take advantage of the unique recognition of mannose-terminated glycoproteins by particular lectins. For example, one may incubate samples suspected of containing HCV viriors or proteins with biotin or avidin-labeled lectins, and precipitate the protein-lectin complex using avidin or biotin. One may also use lectin affinity for HCV proteins to target compounds to virions for therapeutic use, for example by conjugating an antiviral compound to GNA. Alternatively, one may use suitable lectins to remove mannose-terminated glycoproteins from serum or plasma fractions, thus reducing or eliminating the risk of HCV contamination.

It is presently preferred to isolate E1 and/or E2 asialoglycoproteins from crude cell lysates by incubation with an immobilized mannose-binding protein, particularly a lectin such as ConA or GNA. Cells are lysed, e.g., by mechanical disruption in a hypotonic buffer followed by centrifugation to prepare a post-nuclear lysate, and further centrifuged to obtain a crude microsomal membrane fraction. The crude membrane fraction is subsequently solubilized in a buffer containing a detergent, such as Triton X-100, NP40, or the like. This detergent extract is further clarified of insoluble particulates by centrifugation, and the resulting clarified lysate incubated in a chromatography column comprising an immobilized mannose-binding protein, preferably GNA bound to a solid support such as agarose or Sepharose® for a period of time sufficient for binding, typically 16 to 20 hours. The suspension is then applied to the column until E1/E2 begins to appear in the eluent, then incubated in the column for a period of time sufficient for binding, typically about 12–24 hours. The bound material is then washed with additional buffer containing detergent (e.g., Triton X-100, NP40, or the like), and eluted with mannose to provide purified asialoglycoprotein. On elution, it is preferred to elute only until protein begins to appear in the eluate, at which point elution is halted and the column permitted to equilibrate for 2–3 hours before proceeding with elution of the protein. This is believed to allow sufficient time for the slow off-rate expected of large protein aggregates. In cases wherein E1 and E2 are expressed together in native form (i.e., without truncation of the membrane-binding domain), a substantial fraction of the asialoglycoproteins appear as E1:E2 aggregates. When examined by electron microscopy, a significant portion of these aggregates appear as roughly spherical particles having a diameter of about 40 nm, which is the size expected for intact virus. These particles appear to be self-assembling subviral particles. These aggregates are expected to exhibit a quaternary structure very similar to the structure of authentic HCV virion particles, and thus are expected to serve as highly immunogenic vaccines.

The E1/E2 complexes may be further purified by gel chromatography on a basic medium, for example, Fractogel-DEAE or DEAE-Sepharose®. Using Fractogel-DEAE gel chromatography, one may obtain E1/E2 complexes of approximately 60–80% purity. One may further purify E1 by treatment with lysine protease, because E1 has 0–1 Lys residues. Treatment of the complex with lysine protease destroys E2, and permits facile separation of E1.

The tissue specificity of HCV, in combination with the observation that HCV envelope glycoproteins are mannose-terminated, suggests that the virus employs the mannose receptor or the asialoglycoprotein receptor (ASGR) in order to gain entry into host cells. Mannose receptors are found on macrophages and hepatic sinusoidal cells, while the ASGR is found on parenchymal hepatocytes. Thus, it should be possible to culture HCV by employing host cells which express one or both of these receptors. One may either employ primary cell cultures which naturally express the receptor, using conditions under which the receptor is maintained, or one may transfect another cell line such as HeLa, CHO, COS, and the like, with a vector providing for expression of the receptor. Cloning of the mannose receptor and its transfection and expression in fibroblasts has been demonstrated by M. E. Taylor et al, *J Biol Chem* (1990) 265:12156–62. Cloning and sequencing of the ASGR was described by K. Drickamer et al, *J Biol Chem* (1984) 259:770–78 and M. Spiess et al, *Proc Nat Acad Sci USA* (1985) 82:6465–69; transfection and expression of functional ASGR in rat HTC cells was described by M. McPhaul and P. Berg, *Proc Nat Acad Sci USA* (1986) 83:8863–67 and M. McPhaul and P. Berg, *Mol Cell Biol* (1987) 7:1841–47. Thus, it is possible to transfect one or both receptors into suitable cell lines, such as CHO, COS, HeLa, and the like, and to use the resulting cells as hosts for propagation of HCV in culture. Serial passaging of HCV in such cultures should result in development of attenuated strains suitable for use as live vaccines. It is presently preferred to employ an immortalized cell line transfected with one or both recombinant receptors.

Immunogenic compositions can be prepared according to methods known in the art. The present compositions comprise an immunogenic amount of a polypeptide, e.g., E1, E2, or E1/E2 particle compositions, usually combined with a pharmaceutically acceptable carrier, preferably further comprising an adjuvant. If a "cocktail" is desired, a combination of HCV polypeptides, such as, for example, E1 plus E2 antigens, can be mixed together for heightened efficacy. The virus-like particles of E1/E2 aggregates are expected to provide a particularly useful vaccine antigen. Immunogenic compositions may be administered to animals to induce production of antibodies, either to provide a source of antibodies or to induce protective immunity in the animal.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art.

Preferred adjuvants to enhance effectiveness of the composition include, but are not limited to: aluminum hydroxide (alum), N-acetyl-muramyl-L-threonyl-D-isogluta-mine (thr-MDP) as found in U.S Pat. No. 4,606,918, N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE) and RIBI, which contains three components extracted from bacteria, monophosphoryl lipid A, trehalose dimycolate, and cell wall skeleton (MPL+TDM+CWS) in a 2% squalene/Tween® 80 emulsion. Additionally, adjuvants such as Stimulon (Cambridge Bioscience, Worcester, Mass.) may be used. Further, Complete Freund's Adjuvant (CFA) and Incomplete Freund's Adjuvant (IFA) may be used for non-human applications and research purposes.

The immunogenic compositions typically will contain pharmaceutically acceptable vehicles, such as water, saline, glycerol, ethanol, etc. Additionally, auxiliary substances, such as wetting or emulsifying agents, pH buffering substances, and the like, may be included in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect.

Immunogenic compositions used as vaccines comprise an immunologically effective amount of the HCV polypeptide, as well as any other of the above-mentioned components, as needed. "Immunologically effective amount", means that the administration of that amount to an individual, either in a single dose or as part of a series, is effective for treatment, as defined above. This amount varies depending upon the health and physical condition of the individual to be treated, the taxonomic group of individual to be treated (e.g., non-human primate, primate, etc.), the capacity of the individual's immune system to synthesize antibodies, the degree of protection desired, the formulation of the vaccine, the treating doctor's assessment of the medical situation, the strain of infecting HCV, and other relevant factors. It is expected that the amount will fall in a relatively broad range that can be determined through routine trials.

The self-assembling E1/E2 aggregates may also serve as vaccine carriers to present heterologous (non-HCV) haptens, in the same manner as Hepatitis B surface antigen (See European Patent Application 174,444). In this use, the E1/E2 aggregates provide an immunogenic carrier capable of stimulating an immune response to haptens or antigens conjugated to the aggregate. The antigen may be conjugated either by conventional chemical methods, or may be cloned into the gene encoding E1 and/or E2 at a location corresponding to a hydrophilic region of the protein.

The immunogenic compositions are conventionally administered parenterally, typically by injection, for example, subcutaneously or intramuscularly. Additional formulations suitable for other modes of administration include oral formulations and suppositories. Dosage treatment may be a single dose schedule or a multiple dose schedule. The vaccine may be administered in conjunction with other immunoregulatory agents.

C. EXAMPLES

The examples presented below are provided as a further guide to the practitioner of ordinary skill in the art, and are not to be construed as limiting the invention in any way.

Example 1

(Cloning and Expression)

(A) Vectors were constructed from plasmids containing the 5' portion of the HCV genome, as described in EP 318,216 and EP 388,232. Cassette HCV(S/13) contains a StuI-BglII DNA fragment encoding the 5' end of the polyprotein from $Met_1$ up to $Leu_{906}$, beginning at nucleotide −63 relative to $Met_1$. This includes the core protein (C), the E1 protein (also sometimes referred to as S), the E2 protein (also referred to as NS1), and a 5' portion of the NS2a region. Upon expression of the construct, the individual C, E1 and E2 proteins are produced by proteolytic processing.

Cassette HCV(A/B) contains a ApaLI-BglII DNA fragment encoding the 5' end of the polyprotein from $Met_1$ up to $Leu_{906}$, beginning at nucleotide −6 relative to $Met_1$. This includes the core protein (C), the E1 protein (also sometimes referred to as S), the E2 protein (also referred to as NSI), and a 5' portion of the NS2a region. Upon expression of the construct, the individual C, E1 and E2 proteins are produced by proteolytic processing.

Cassette C-E1 (S/B) (a StuI-BamHI portion) contains the 5' end from $Met_1$ up to $Ile_{340}$, (a BamHI site in the gene). Expression of this cassette results in expression of C and a somewhat truncated E1 (E1'). The portion truncated from the 3' end is a hydrophobic region believed to serve as a translocation signal.

Cassette NS 1 (B/B) (a BamHI-BglII portion) contains a small 3' portion of E1 (from $Met_{364}$), all of E2, and a portion of NS2a (to $Leu_{906}$). In this construct, the E1 fragment serves as a translocation signal.

Cassette TPA-NS1 employs a human tissue plasminogen activator (tPA) leader as a translocation signal instead of the 3' portion of E1. The cassette contains a truncated form of E2, from $Gly_{406}$ to $Glu_{661}$ in which the hydrophobic 3' end is deleted.

Each cassette was inserted into the vector pGEM3Z (Promega) with and without a synthetic β-globin 5' non-coding sequence for transcription and translation using T7 and rabbit reticulocyte expression in vitro. Recombinant vaccinia virus (rVV) vectors were prepared by inserting the cassettes into the plasmid pSC11 (obtained from Dr. B. Moss, NIH) followed by recombination with vaccinia virus, as described by Charkrabarty et al, *Mol Cell Biol* (1985) 5:3403–09.

(B) An alternate expression vector was constructed by inserting HCV(A/B) between the StuI and SpeI sites of pSC59 (obtained from Dr. B. Moss, NIH) followed by recombination with vaccinia virus, as described by Charkrabarty et al, *Mol Cell Biol* (1985) 5:3403–09.

(C) HeLa S3 cells were collected by centrifugation for 7 minutes at 2000 rpm at room temperature in sterile 500 ml centrifuge bottles (JA-10 rotor). The pellets were resuspended at a final concentration of $2\times10^7$ cells/ml in additional culture medium (Joklik modified MEM Spinner medium +5% horse serum and Gentamycin) ("spinner medium"). Sonicated crude vv/SC59-HCV virus stock was added at a multiplicity of infection of 8 pfu/cell, and the mixture stirred at 37° C. for 30 minutes. The infected cells were then transferred to a spinner flask containing 8 liters spinner medium and incubated for 3 days at 37° C.

The cultured cells were then collected by centrifugation, and the pellets resuspended in buffer (10 mM Tris-HCl, pH 9.0, 15 ml). The cells were then homogenized using a 40 ml Dounce Homogenizer (50 strokes), and the nuclei pelleted by centrifugation (5 minutes, 1600 rpm, 4° C., JA-20 rotor). The nuclear pellets were resuspended in Tris buffer (4 ml), rehomogenized, and pelleted again, pooling all supernatants.

The pooled lysate was divided into 10 ml aliquots and sonicated 3×30 minutes in a cuphorn sonicator at medium power. The sonicated lysate (15 ml) was layered onto 17 ml sucrose cushions (36%) in SW28 centrifuge tubes, and centrifuged at 13,500 rpm for 80 minutes at 4° C. to pellet the virus. The virus pellet was resuspended in 1 ml of Tris buffer (1 mM Tris-HCl, pH 9.0) and frozen at −80° C.

Example 2

(Comparison of In Vitro and In Vivo Products)

(A) E1 and E2 were expressed both in vitro and in vivo and $^{35}$S-Met labeled using the vectors described in Example 1 above. BSC-40 and HeLa cells were infected with the rVV vectors for in vivo expression. Both the medium and the cell lysates were examined for recombinant proteins. The products were irnmunoprecipitated using human HCV immune serum, while in vitro proteins were analyzed directly. The resulting proteins were analyzed by SDS-PAGE.

The reticulocyte expression system (pGEM3Z with HCV (S/B) or HCV(A/B)) produced C, E1 and E2 proteins having molecular weights of approximately 18 kD, 35 kD, and 72 kD, respectively. Lysates from BSC-40 and HeLa cells transfected with rVV containing HCV(S/B), HCV(A/B) or C-E1 (S/B) exhibited the same proteins. Because the reticulocyte system does not provide efficient golgi processing and therefore does not provide sialic acid, the fact that both in vitro and in vivo products exhibited identical mobilities suggests that the proteins are not sialylated in vivo. Only the rVV vector containing TPA-NS1 resulted in any extracellular secretion of E2, which exhibited an altered mobility consistent with sialylation.

(B) HCV(S/B) was expressed in vitro and incubated with a panel of biotinylated lectins: GNA, SNA, PNA, WGA, and ConA. Following incubation, the complexes were collected on avidin-acrylic beads, washed, eluted with Laemmli sample buffer, and analyzed by SDS-PAGE. The results showed that E1 and E2 bound to GNA and ConA, which indicates the presence of mannose. GNA binds to terminal mannose groups, while ConA binds to any α-linked mannose. The lack of binding to SNA, PNA, and WGA indicates that none of the proteins contained sialic acid, galactose-N-acetylgalactosamine, or N-acetylglucosamine.

(C) Radiolabeled E1 and E2 were produced in BSC-40 cells by infection with rVV containing HCV(S/B) (vv/SC 11-HCV), and immunoprecipitated with human HCV$^+$ immune serum. One half of the immunoprecipitated material was treated overnight with neuraminidase to remove any sialic acid. Following treatment, the treated and untreated proteins were analyzed by SDS-PAGE. No significant difference in mobility was observed, indicating lack of sialylation in vivo.

(D) Radiolabeled E1 and E2 were produced in BSC-40 cells by infection with rVV containing HCV(A/B) (vv/SC59-HCV), and either immunoprecipitated with human HCV$^+$ serum, or precipitated using biotinylated GNA lectin linked to acrylic beads, using vv/SC 11 free of HCV sequences as control. The precipitates were analyzed by SDS-PAGE. The data demonstrated that E1 and E2 were the major species of mannose-terminated proteins in vv/SC59-HCV infected cells. GNA was as efficient as human antisera in precipitating E1 and E2 from cell culture medium. A 25 kD component was observed, but appears to be specific to vaccinia-infected cells.

Example 3

(Purification Using Lectin)

(A) HeLa S3 cells were inoculated with purified high-titer vv/SC59-HCV virus stock at a multiplicity of infection of 5 pfu/cell, and the mixture stirred at 37° C. for 30 minutes. The infected cells were then transferred to a spinner flask containing 8 liters spinner medium and incubated for 3 days at 37° C. The cells were collected again by centrifugation and resuspended in hypotonic buffer (20 mM HEPES, 10 mM NaCl, 1 mM $MgCl_2$, 120 ml) on ice. The cells were then homogenized by Dounce Homogenizer (50 strokes), and the nuclei pelleted by centrifugation (5 minutes, 1600 rpm, 4° C., JA-20 rotor). The pellets were pooled, resuspended in 48 ml hypotonic buffer, rehomogenized, recentrifuged, pooled again, and frozen at −80° C.

The frozen supernatants were then thawed, and the microsomal membrane fraction of the post-nuclear lysate isolated by centrifuging for 20 minutes in a JA-20 rotor at 13,500 rpm at 4° C. The supernatant was removed by aspiration.

The pellets were taken up in 96 ml detergent buffer (20 mM Tris-HCl, 100 mM NaCl, 1 mM EDTA, 1 mM DDT, 0.5% Triton X-100, pH 7.5) and homogenized (50 strokes). The product was clarified by centrifugation for 20 minutes at 13,500 rpm, 4° C., and the supernatants collected.

A GNA-agarose column (1 cm×3 cm, 3 mg GNA/ml beads, 6 ml bed volume, Vector Labs, Burlingame, CA) was pre-equilibrated with detergent buffer. The supernatant sample was applied to the column with recirculation at a flow rate of 1 ml/min for 16–20 hours at 4° C. The column was then washed with detergent buffer.

The purified E1/E2 proteins were eluted with α-D-mannoside (0.9 M in detergent buffer) at a flow rate of 0.5 ml/minute. Elution was halted at the appearance of E1/E2 in the eluent, and the column allowed to reequilibrate for 2–3 hours. Fractions were analyzed by Western blot and silver staining. Peak fractions were pooled and UV-irradiated to inactivate any residual vaccinia virus.

(B) GNA-agarose purified E1 and E2 asialoglycoproteins were sedimented through 20–60% glycerol gradients. The gradients were fractionated and proteins were analyzed by SDS-PAGE and western blotting. Blots were probed with GNA for identification of E1 and E2. The results indicate the presence of a E1:E2 heterodimer which sediments at the expected rate (i.e., a position characteristic of a 110 kD protein). Larger aggregates of HCV envelope proteins also are apparent. E2:E2 homodimers also were apparent. E2 appeared to be over-represented in the larger species relative to E1, although discrete E1:E2 species also were detected. The larger aggregates sedimented significantly faster than the thyroglobulin marker.

(C) GNA-agarose purified E1 and E2 were sedimented through 20–60% glycerol gradients containing 1 mM EDTA. Fractions were analyzed by SDS-PAGE with and without β-mercaptoethanol (βME). Little or no difference in the apparent abundance of E1 and E2 in the presence or absence of OME was observed, indicating the absence of disulfide links between heterodimers.

(D) E1/E2 complexes (approximately 40% pure) were analyzed on a Coulter DM-4 sub-micron particle analyzer. Material in the 20–60 nm range was detected.

(E) E1/E2 complexes (approximately 40% pure) were analyzed by electron microscopy using negative staining with phosphotungstic acid. The electron micrograph revealed the presence of particles having a spherical appearance and a diameter of about 40 nm. E1/E2 complexes were incubated with HCV$^+$ human immune serum, then analyzed by EM with negative staining. Antibody complexes containing large aggregates and smaller particles were observed.

Example 4

(Chromatographic Purification)

(A) The GNA lectin-purified material prepared as described in Example 3 (0.5–0.8 ml) was diluted 10× with buffer A (20 mM Tris-Cl buffer, pH 8.0, 1 mM EDTA), and applied to a 1.8×1.5 cm column of Fractogel EMD DEAE-650 (EM Separations, Gibbstown, N.J., cat. no. 16883) equilibrated in buffer A. The protein fraction containing E1/E2 was eluted with the same buffer at a flow rate of 0.2 ml/minute, and 1 ml fractions collected. Fractions containing E1 and E2 (determined by SDS-PAGE) were pooled and stored at −80° C.

(B) The material purified in part (A) above has a purity of 60–80%, as estimated by SDS-PAGE. The identification of the putative E1 and E2 bands was confirmed by N-terminal sequence analysis after using a transfer technique. For the purpose, the fractogel-DEAE purified E1/E2 material was reduced by addition of Laemmli buffer (pH 6.8, 0.06 M Tris-Cl, 2.3% SDS, 10% glycerol, 0.72 M β-mercaptoethanol) and boiled for 3 minutes. The sample was then loaded onto a 10% polyacrylamide gel. After SDS-PAGE, the protein was transferred to a polyvinylidene difluoride (PVDF) 0.2 μm membrane (Bio-Rad Laboratories, Richmond, Calif.). The respective putative E1 and E2 protein bands were excised from the blot and subjected to N-terminal amino acid analysis, although no special care was taken to prevent amino-terminal blockage during preparation of the material. The first 15 cycles revealed that the E1 sample had a sequence Tyr-Gln-Val-Arg-X-Ser-Thr-Gly-X-Tyr-His-Val-X-Asn-Asp, SEQ ID No: 2 while the sequence of E2 was Thr-His-Val-Thr-Gly-X-X-Ala-Gly-His-X-Val-X-Gly-Phe SEQ ID No: 2. This amino acid sequence data is in agreement with that expected from the corresponding DNA sequences.

The E1/E2 product purified above by fractogel-DEAE chromatography is believed to be aggregated as evidenced by the fact that a large amount of E1 and E2 coelutes in the void volume region of a gel permeation chromatographic Bio-Sil TSK-4000 SW column. This indicates that under native conditions a significant amount of the E1/E2 complex has a molecular weight of at least 800 kD. E1/E2 material having a molecular weight of about 650 kD was also observed.

Example 5

(Additional Cloning and Expression)

(A) The following cassettes containing 5' portions of the HCV polyprotein were inserted into the vector pGEM4Z (Promega) with and without a synthetic yellow fever virus 5' non-coding sequence and also into recombinant vaccinia virus (rVV) vectors (as described in Example 1A). Cassette C5p-l contains a fragment encoding the 5' end of the polyprotein from $Met_1$ to $Trp_{1079}$, beginning at nucleotide −275 relative to $Met_1$, with EcoRI linkers on the 5' and 3' ends. Cassette C5p-3 contains an fragment encoding the 5' end of the polyprotein from $Met_1$ to $Trp_{,1079}$, with EcoRI linkers on the 5' and 3' ends. Both cassettes encode C, E1 and E2 proteins and a 5' portion of the NS2 protein.

(B) The following cassettes containing 5' portions of the HCV polyprotein were inserted into the vector pSC59 followed by recombination with vaccinia virus (described in Example 1B). Cassette HCV(Poly) contains a blunt-ended StuI-BglII fragment encoding the 5' end of the polyprotein from $Met_1$ to $Asp_{966}$ beginning at nucleotide −65 relative to $Met_1$. This construct expresses C, E1 and E2 proteins, and a 5' portion of the NS2 protein.

Cassette HCV(5C/SB) contains a blunt-ended StuI-BamHI fragment encoding the 5' end of the polyprotein from $Met_1$ to $Ile_{340}$ beginning at nucleotide −65 relative to $Met_1$. This construct expresses the C protein and a truncated E1 protein. Cassette HCV(6C/SS) contains a SalI (blunted)-EcoRI fragment encoding the 5' end of the polyprotein from $Met_1$ to $Asp_{382}$ wherein $Ser_2$ is replaced with $Gly_2$. This construct expresses the C protein and a truncated E1 protein.

Cassette HCV(E12C/B) contains a blunt-ended ClaI-BglII fragment encoding a portion of the polyprotein from $Met_{134}$ to $Asp_{966}$ inserted into an EcoRI blunted SC59 vector.

Cassette HCV(E1/S) contains a blunt-ended ClaI/SalI fragment encoding a portion of the polyprotein from $Met_{134}$ to $Val_{381}$ inserted into an EcoRi blunted SC59 vector.

(C) HeLa S3 cells were collected by centrifugation for 7 minutes at 2000 rpm at 4° C. in sterile 250 ml centrifuge bottles. The pellets were resuspended at a final concentration of 5×106 cells/ml in Gey's balanced Salt Solution (GBSS). Sonicated crude vv/SC59-HCV virus stock was added at a multiplicity of infection of 0.5 pfu/cell, and the mixture stirred at 37° C. for 1–2 hours. The infected cells were then transferred at a final concentration of 106 cells/ml to a spinner flask containing I liter culture medium (Joklik MEM+10% fetal bovine serum+non-essential amino acids, vitamins, pen/strep) and incubated for 3 days at 37° C.

The cultured cells were then collected by centrifugation, and the pellets resuspended in buffer (10 mM Tris-HCl, pH 9.0, 15 ml). The cells were then homogenized using a 40 ml Dounce Homogenizer (50 strokes), and the nuclei pelleted by centrifugation (5 minutes, 1600 rpm, 4° C., JA-20 rotor). The nuclear pellets were resuspended in Tris buffer (4 ml), rehomogenized, and pelleted again, pooling all supernatants.

The pooled lysate was divided into 5 ml aliquots, and 0.1 volume of 2.5 mg/ml trypsin added and incubated at 37° C. for 30 minutes. The aliquots were then sonicated 3×30 seconds in a cuphorn sonicator at medium power. The sonicated lysate was used as the crude stock.

Example 6

(Additional Comparison of In Vitro and In Vivo Products)

(A) E1 and E2 were expressed both in vitro and in vivo and $^{35}S$-Met labeled using the vectors described in Example 5 above and the procedures described in Example 2 above. BSC-40 and HeLa cells were infected with the rVV vectors for in vivo expression. Both the medium and the cell lysates were examined for recombinant proteins. The products were immunoprecipitated using human HCV immune serum or rabbit or goat anti-HCV antiserum, while in vitro proteins were analyzed directly. The resulting proteins were analyzed by SDS-PAGE and EndoH digestion.

Example 7

(Additional Lectin Purification)

(A) HeLa S3 cells were inoculated with purified high-titer vv/SC59-HCV virus stock (HCV(Poly) or HCV(E12C/B) as described in Example 5 above) at a multiplicity of infection of 1 pfu/cell, and the mixture stirred at 37° C. for 1–2 hours. The infected cells were then transferred to spinner flasks containing 1 liter culture medium (see Example 5, supra) and incubated for 2 days at 37° C. A total of 10 liters of cells were collected by centrifugation and resuspended in hypotonic buffer (20 mM HEPES, 10 mM NaCl, 1 mM $MgCl_2$, 120 ml) containing protease inhibitors (PMSF and pepstatin A) on ice. The cells were then homogenized in a 40 ml homogenizer in two batches, pelleted by centrifugation (20 minutes, 12,000 rpm), and re-suspended and re-homogenized. Each pellet was resuspended in approximately 10 ml 25 mM $NaPO_4$ (pH 6.8) in a homogenizer, and an equal volume of 4% Triton X-100 in 100 mM $NaPO_4$ (pH 6.8) added. The pelleted cells were homogenized with 20 strokes, spun at 12,000 rpm for 15 minutes (4 tubes/pellet), and the supernatant saved. The resuspension, Triton addition and centrifugation steps were repeated, and the saved supernatants combined, and frozen at –80° C.

The frozen supernatants were thawed, spun at 12,000 rpm for 15 minutes, combined and held at 4° C. A GNA-agarose column (1 cm×3 cm, 3 mg GNA/ml beads, 6 ml bed volume, Vector Labs, Burlingame, Calif.) was pre-equilibrated with detergent buffer (2% Triton X-100 in 50 mM $NaPO_4$, pH 6.8). The supernatant sample was applied to the column with recirculation at a flow rate of 1 ml/min for 16–20 hours at 4° C. The column was then washed with detergent buffer, followed by 30 ml each of: Buffer A (1M NaCl, 20 mM $NaPO_4$ (pH 6.0), 0.1% Triton X-100); Buffer B (20 mM $NaPO_4$ (pH 6.0), 0.1% Triton X-100); Buffer D (0.2M methyl-α-D-mannopyranoside (mmp), 20 mM $NaPO_4$ (pH 6.0), 0.1% Triton X-100); Buffer E (1M mmp, 20 mM $NaPO_4$ (pH 6.0), 0.1% Triton X-100); Buffer F (1M mmp, 1M NaCl, 20 mM $NaPO_4$ (pH 6.0), 0.1% Triton X-100). Purified E1/E2 proteins come off as eluted material in Buffers D and E, which were collected separately and analyzed by SDS-PAGE.

Example 8

(Additional Chromatographic Purification)

(A) The GNA lectin-purified material prepared as described in Example 7 was applied to a column of S-Sepharose Fast Flow (Pharmacia) equilibrated in buffer B (see Example 7). The column was washed with Buffer B, then eluted with Buffer 1 (0.5M NaCl, 20 mM $NaPO_4$ (pH 6.0), 0.1% Triton X-100) and Buffer 2 (1M NaCl, 20 mM $NaPO_4$ (pH 6.0), 0.1% Triton X-100). Fractions containing E1 and E2 (determined by SDS-PAGE) were pooled and stored at –80° C.

---

What is claimed:

1. A hepatitis C virus (HCV) glycoprotein composition comprising a pharmaceutically acceptable excipient and a purified HCV E1/E2 glycoprotein aggregate, wherein said glycoproteins of said aggregate have mannose-terminated glycosylation, wherein less than about 10% of the total N-linked carbohydrate on said glycoproteins is sialic acid, and further wherein said aggregate comprises a glycoprotein expressed from the E1 region of HCV and a glycoprotein expressed from the E2 region of HCV, said aggregate produced by the method comprising the steps of:

contacting a composition containing HCV glycoproteins with a mannose-binding protein specific for mannose-terminated glycoproteins; and isolating the portion of the composition which binds to said mannose-binding protein.

2. The composition of claim 1 wherein said mannose-binding protein is a lectin.

3. The composition of claim 2 wherein said lectin is Galanthus nivalus agglutinin.

4. A composition comprising a pharmaceutically acceptable excipient and a purified hepatitis C virus (HCV) glycoprotein having mannose-terminated glycosylation, wherein less than about 10% of the total N-linked carbohydrate on said HCV glycoprotein is sialic acid, wherein said HCV glycoprotein is selected from the group consisting of a glycoprotein expressed from the E1 region of HCV and a glycoprotein expressed from the E2 region of HCV, produced by the method comprising the steps of:

growing a mammalian host cell transformed with a structural gene encoding said HCV glycoprotein in a suitable culture medium, wherein said structural gene is linked to a sequence encoding a secretion leader that directs the glycoprotein to the endoplasmic reticulum;

causing expression of said structural gene and secretion leader sequence under conditions inhibiting sialylation, wherein said conditions inhibiting sialylation comprise inhibiting transport of glycoproteins from the endoplasmic reticulum to the golgi; and isolating said HCV glycoprotein from said cell culture by contacting said HCV glycoprotein with a mannose-binding protein specific for mannose-terminated glycoproteins, and isolating the protein which binds to said mannose-binding protein.

5. The composition of claim 4, wherein said qlycoprotein is expressed from the E1 region of HCV.

6. The composition of claim 4, wherein said glycoprotein is expressed from the E2 region of HCV.

7. The composition of claim 4, wherein said mannose-binding protein is a lectin.

8. The composition of claim 5, wherein said mannose-binding protein is a lectin.

9. The composition of claim 6, wherein said mannose-binding protein is a lectin.

10. A method of inducing an immune response in an animal, which method comprises:

providing an effective amount of a composition according to claim 4; and administering said composition to said animal.

11. The method of claim 10, wherein said HCV glycoprotein is expressed from the E1 region of HCV.

12. The method of claim 10, wherein said HCV glycoprotein is expressed from the E2 region of HCV.

13. The method of claim 10, wherein said HCV glycoprotein is an E1/E2 aggregate.

14. The method of claim 10, wherein said animal is a primate.

15. An isolated hepatitis C virus (HCV) glycoprotein having mannose-terminated glycosylation, wherein less than about 10% of the total N-linked carbohydrate on said HCV glycoprotein is sialic acid, wherein said HCV glycoprotein is selected from the group consisting of a glycoprotein expressed from the E1 region of HCV, a glycoprotein expressed from the E2 region of HCV, and an E1/E2 aggregate glycoprotein, wherein said glycoprotein is produced by the method comprising the steps of:

growing a mammalian host cell transformed with a structural gene encoding said glycoprotein in a suitable culture medium, wherein said structural gene is linked to a sequence encoding a secretion leader that directs the glycoprotein to the endoplasmic reticulum;

causing expression of said structural gene and secretion leader sequence under conditions inhibiting sialylation, wherein said conditions inhibiting sialylation comprise inhibiting transport of glycoproteins from the endoplasmic reticulum to the golgi; and isolating said HCV glycoprotein from said cell culture by contacting said HCV glycoprotein with a mannose-binding protein specific for mannose-terminated glycoproteins.

16. The HCV glycoprotein of claim 15 wherein said conditions inhibiting sialylation comprise expression of the glycoprotein at a rate sufficient to inhibit transport of the glycoprotein from the endoplasmic reticulum to the golgi.

17. The HCV glycoprotein of claim 15 wherein said conditions inhibiting sialylation further comprise a sufficient amount of a calcium modulator to cause release of proteins within the host cell's endoplasmic reticulum.

18. The HCV glycoprotein of any of claims 15–17, wherein said glycoprotein is expressed from the E1 region of HCV.

19. The HCV glycoprotein of any of claims 15–17, wherein said glycoprotein is expressed from the E2 region of HCV.

20. The HCV glycoprotein of any of claims 15–17, wherein said glycoprotein is an E1/E2 aggregate.

21. The HCV glycoprotein of any of claims 15–17, wherein said glycoprotein is an E1/E1 aggregate.

22. The HCV glycoprotein of any of claims 15–17, wherein said glycoprotein is an E2/E2 aggregate.

23. An isolated hepatitis C virus (HCV) E1/E2 glycoprotein aggregate having mannose-terminated glycosylation, wherein less than about 10% of the total N-linked carbohydrate on said HCV glycoprotein is sialic acid, and further wherein said HCV glycoprotein aggregate comprises a glycoprotein expressed from the E1 region of HCV and a glycoprotein expressed from the E2 region of HCV, wherein said glycoprotein aggregate is produced by the method comprising the steps of:

growing a host cell transformed with a structural gene encoding said glycoprotein in a suitable culture medium;

causing expression of said structural gene under conditions inhibiting sialylation; and isolating said HCV glycoprotein aggregate from said cell culture by contacting said HCV glycoprotein with a mannose-binding protein specific for mannose-terminated glycoproteins.

24. A method of inducing an immune response in an animal, which methods comprises:

providing an effective amount of a composition according to claim 1; and administering said composition to said animal.

25. The method of claim 24, wherein said animal is a primate.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

Tyr Gln Val Arg Xaa Ser Thr Gly Xaa Tyr His Val Xaa Asn Asp
1            5                  10                15

(2) INFORMATION FOR SEQ ID NO:2:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Thr His Val Thr Gly Xaa Xaa Ala Gly His Xaa Val Xaa Gly Phe
1            5                  10                15

```
(2) INFORMATION FOR SEQ ID NO:3:

(i) SEQUENCE CHARACTERISTICS:
        (A) LENGTH: 2955 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 9
        (D) OTHER INFORMATION: /note= "There is a heterogeneity at
            this location; Xaa = Arg or Lys"

(ix) FEATURE:
        (A) NAME/KEY: Modified-site
        (B) LOCATION: 11
        (D) OTHER INFORMATION: /note= "There is a heterogeneity at
            this location; Xaa = Asn or Thr"

(ix) FEATURE:
        (A) NAME/KEY: Modified-site
        (B) LOCATION: 176
        (D) OTHER INFORMATION: /note= "There is a heterogeneity at
            this location; Xaa = Ile or Thr"

(ix) FEATURE:
        (A) NAME/KEY: Modified-site
        (B) LOCATION: 334
        (D) OTHER INFORMATION: /note= "There is a heterogeneity at
            this location; Xaa = Met or Val"

(ix) FEATURE:
        (A) NAME/KEY: Modified-site
        (B) LOCATION: 603
        (D) OTHER INFORMATION: /note= "There is a heterogeneity at
            this location; Xaa = Ile or Leu"

(ix) FEATURE:
        (A) NAME/KEY: Modified-site
        (B) LOCATION: 848
        (D) OTHER INFORMATION: /note= "There is a heterogeneity at
            this location; Xaa = Asn or Tyr"

(ix) FEATURE:
        (A) NAME/KEY: Modified-site
        (B) LOCATION: 1114
        (D) OTHER INFORMATION: /note= "There is a heterogeneity at
            this location; Xaa = Pro or Ser"

(ix) FEATURE:
        (A) NAME/KEY: Modified-site
        (B) LOCATION: 1117
        (D) OTHER INFORMATION: /note= "There is a heterogeneity at
            this location; Xaa = Ser or Thr"

(ix) FEATURE:
        (A) NAME/KEY: Modified-site
        (B) LOCATION: 1276
        (D) OTHER INFORMATION: /note= "There is a heterogeneity at
            this location; Xaa = Leu or Pro"

(ix) FEATURE:
        (A) NAME/KEY: Modified-site
        (B) LOCATION: 1454
        (D) OTHER INFORMATION: /note= "There is a heterogeneity at
            this location; Xaa = Cys or Tyr"

(ix) FEATURE:
        (A) NAME/KEY: Modified-site
        (B) LOCATION: 1471
        (D) OTHER INFORMATION: /note= "There is a heterogeneity at
            this location; Xaa = Ser or Thr"

(ix) FEATURE:
        (A) NAME/KEY: Modified-site
        (B) LOCATION: 1877
```

```
              (D) OTHER INFORMATION: /note= "There is a heterogeneity at
                  this location; Xaa = Glu or Gly"

(ix) FEATURE:
              (A) NAME/KEY: Modified-site
              (B) LOCATION: 1948
              (D) OTHER INFORMATION: /note= "There is a heterogeneity at
                  this location; Xaa = His or Leu"

(ix) FEATURE:
              (A) NAME/KEY: Modified-site
              (B) LOCATION: 1949
              (D) OTHER INFORMATION: /note= "There is a heterogeneity at
                  this location; Xaa = Cys or Ser"

(ix) FEATURE:
              (A) NAME/KEY: Modified-site
              (B) LOCATION: 2021
              (D) OTHER INFORMATION: /note= "There is a heterogeneity at
                  this location; Xaa = Gly or Val"

(ix) FEATURE:
              (A) NAME/KEY: Modified-site
              (B) LOCATION: 2349
              (D) OTHER INFORMATION: /note= "There is a heterogeneity at
                  this location; Xaa = Ser or Thr"

(ix) FEATURE:
              (A) NAME/KEY: Modified-site
              (B) LOCATION: 2385
              (D) OTHER INFORMATION: /note= "There is a heterogeneity at
                  this location; Xaa =Phe or Tyr"

(ix) FEATURE:
              (A) NAME/KEY: Modified-site
              (B) LOCATION: 2386
              (D) OTHER INFORMATION: /note= "There is a heterogeneity at
                  this location; Xaa = Ala or Ser"

(ix) FEATURE:
              (A) NAME/KEY: Modified-site
              (B) LOCATION: 2502
              (D) OTHER INFORMATION: /note= "There is a heterogeneity at
                  this location; Xaa = Phe or Leu"

(ix) FEATURE:
              (A) NAME/KEY: Modified-site
              (B) LOCATION: 2690
              (D) OTHER INFORMATION: /note= "There is a heterogeneity at
                  this location; Xaa = Gly or Arg"

(ix) FEATURE:
              (A) NAME/KEY: Modified-site
              (B) LOCATION: 2921
              (D) OTHER INFORMATION: /note= "There is a heterogeneity at
                  this location; Xaa = Arg or Gly"

(xi) SEQUENCE DESCRIPTION: SEQ ID NO:3:

Met Ser Thr Asn Pro Lys Pro Gln Xaa Lys Xaa Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110
```

```
Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Ser Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Xaa
                165                 170                 175

Phe Leu Leu Ala Leu Leu Ser Cys Leu Thr Val Pro Ala Ser Ala Tyr
                180                 185                 190

Gln Val Arg Asn Ser Thr Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
                245                 250                 255

Gln Leu Arg Arg His Ile Asp Leu Leu Val Gly Ser Ala Thr Leu Cys
        260                 265                 270

Ser Ala Leu Tyr Val Gly Asp Leu Cys Gly Ser Val Phe Leu Val Gly
    275                 280                 285

Gln Leu Phe Thr Phe Ser Pro Arg Arg His Trp Thr Thr Gln Gly Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Xaa Ala Gln
                325                 330                 335

Leu Leu Arg Ile Pro Gln Ala Ile Leu Asp Met Ile Ala Gly Ala His
        340                 345                 350

Trp Gly Val Leu Ala Gly Ile Ala Tyr Phe Ser Met Val Gly Asn Trp
    355                 360                 365

Ala Lys Val Leu Val Val Leu Leu Phe Ala Gly Val Asp Ala Glu
370                 375                 380

Thr His Val Thr Gly Gly Ser Ala Gly His Thr Val Ser Gly Phe Val
385                 390                 395                 400

Ser Leu Leu Ala Pro Gly Ala Lys Gln Asn Val Gln Leu Ile Asn Thr
                405                 410                 415

Asn Gly Ser Trp His Leu Asn Ser Thr Ala Leu Asn Cys Asn Asp Ser
        420                 425                 430

Leu Asn Thr Gly Trp Leu Ala Gly Leu Phe Tyr His His Lys Phe Asn
    435                 440                 445

Ser Ser Gly Cys Pro Glu Arg Leu Ala Ser Cys Arg Pro Leu Thr Asp
    450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Pro Lys Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
    515                 520                 525
```

-continued

Trp Gly Glu Asn Asp Thr Asp Val Phe Val Leu Asn Asn Thr Arg Pro
530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Ala Gly Asn
                565                 570                 575

Asn Thr Leu His Cys Pro Thr Asp Cys Phe Arg Lys His Pro Asp Ala
            580                 585                 590

Thr Tyr Ser Arg Cys Gly Ser Gly Pro Trp Xaa Thr Pro Arg Cys Leu
        595                 600                 605

Val Asp Tyr Pro Tyr Arg Leu Trp His Tyr Pro Cys Thr Ile Asn Tyr
    610                 615                 620

Thr Ile Phe Lys Ile Arg Met Tyr Val Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Thr Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Lys Trp Val Pro
    770                 775                 780

Gly Ala Val Tyr Thr Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Leu Trp Trp Leu Gln Xaa
        835                 840                 845

Phe Leu Thr Arg Val Glu Ala Gln Leu His Val Trp Ile Pro Pro Leu
    850                 855                 860

Asn Val Arg Gly Gly Arg Asp Ala Val Ile Leu Leu Met Cys Ala Val
865                 870                 875                 880

His Pro Thr Leu Val Phe Asp Ile Thr Lys Leu Leu Leu Ala Val Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Phe Cys Ala Leu Ala Arg Lys Met
        915                 920                 925

Ile Gly Gly His Tyr Val Gln Met Val Ile Lys Leu Gly Ala Leu
930                 935                 940

-continued

```
Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Gln Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Arg
        995                1000                1005

Glu Ile Leu Leu Gly Pro Ala Asp Gly Met Val Ser Lys Gly Trp Arg
   1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
                1045                1050                1055

Gly Glu Val Gln Ile Val Ser Thr Ala Ala Gln Thr Phe Leu Ala Thr
            1060                1065                1070

Cys Ile Asn Gly Val Cys Trp Thr Val Tyr His Gly Ala Gly Thr Arg
        1075                1080                1085

Thr Ile Ala Ser Pro Lys Gly Pro Val Ile Gln Met Tyr Thr Asn Val
   1090                1095                1100

Asp Gln Asp Leu Val Gly Trp Pro Ala Xaa Gln Gly Xaa Arg Ser Leu
1105                1110                1115                1120

Thr Pro Cys Thr Cys Gly Ser Ser Asp Leu Tyr Leu Val Thr Arg His
                1125                1130                1135

Ala Asp Val Ile Pro Val Arg Arg Arg Gly Asp Ser Arg Gly Ser Leu
            1140                1145                1150

Leu Ser Pro Arg Pro Ile Ser Tyr Leu Lys Gly Ser Ser Gly Gly Pro
        1155                1160                1165

Leu Leu Cys Pro Ala Gly His Ala Val Gly Ile Phe Arg Ala Ala Val
   1170                1175                1180

Cys Thr Arg Gly Val Ala Lys Ala Val Asp Phe Ile Pro Val Glu Asn
1185                1190                1195                1200

Leu Glu Thr Thr Met Arg Ser Pro Val Phe Thr Asp Asn Ser Ser Pro
                1205                1210                1215

Pro Val Val Pro Gln Ser Phe Gln Val Ala His Leu His Ala Pro Thr
            1220                1225                1230

Gly Ser Gly Lys Ser Thr Lys Val Pro Ala Ala Tyr Ala Ala Gln Gly
        1235                1240                1245

Tyr Lys Val Leu Val Leu Asn Pro Ser Val Ala Ala Thr Leu Gly Phe
   1250                1255                1260

Gly Ala Tyr Met Ser Lys Ala His Gly Ile Asp Xaa Asn Ile Arg Thr
1265                1270                1275                1280

Gly Val Arg Thr Ile Thr Thr Gly Ser Pro Ile Thr Tyr Ser Thr Tyr
                1285                1290                1295

Gly Lys Phe Leu Ala Asp Gly Gly Cys Ser Gly Gly Ala Tyr Asp Ile
            1300                1305                1310

Ile Ile Cys Asp Glu Cys His Ser Thr Asp Ala Thr Ser Ile Leu Gly
        1315                1320                1325

Ile Gly Thr Val Leu Asp Gln Ala Glu Thr Ala Gly Ala Arg Leu Val
   1330                1335                1340

Val Leu Ala Thr Ala Thr Pro Pro Gly Ser Val Thr Val Pro His Pro
1345                1350                1355                1360
```

-continued

Asn Ile Glu Glu Val Ala Leu Ser Thr Thr Gly Glu Ile Pro Phe Tyr
                1365                1370                1375

Gly Lys Ala Ile Pro Leu Glu Val Ile Lys Gly Gly Arg His Leu Ile
            1380                1385                1390

Phe Cys His Ser Lys Lys Cys Asp Glu Leu Ala Ala Lys Leu Val
        1395                1400                1405

Ala Leu Gly Ile Asn Ala Val Ala Tyr Tyr Arg Gly Leu Asp Val Ser
    1410                1415                1420

Val Ile Pro Thr Ser Gly Asp Val Val Val Ala Thr Asp Ala Leu
1425                1430                1435                1440

Met Thr Gly Tyr Thr Gly Asp Phe Asp Ser Val Ile Asp Xaa Asn Thr
                1445                1450                1455

Cys Val Thr Gln Thr Val Asp Phe Ser Leu Asp Pro Thr Phe Xaa Ile
            1460                1465                1470

Glu Thr Ile Thr Leu Pro Gln Asp Ala Val Ser Arg Thr Gln Arg Arg
        1475                1480                1485

Gly Arg Thr Gly Arg Gly Lys Pro Gly Ile Asn Arg Phe Val Ala Pro
    1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
                1525                1530                1535

Val Arg Leu Arg Ala Tyr Met Asn Thr Pro Gly Leu Pro Val Cys Gln
            1540                1545                1550

Asp His Leu Glu Phe Trp Glu Gly Val Phe Thr Gly Leu Thr His Ile
        1555                1560                1565

Asp Ala His Phe Leu Ser Gln Thr Lys Gln Ser Gly Glu Asn Leu Pro
    1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
                1605                1610                1615

Thr Leu His Gly Pro Thr Pro Leu Leu Tyr Arg Leu Gly Ala Val Gln
            1620                1625                1630

Asn Glu Ile Thr Leu Thr His Pro Val Thr Lys Tyr Ile Met Thr Cys
        1635                1640                1645

Met Ser Ala Asp Leu Glu Val Val Thr Ser Thr Trp Val Leu Val Gly
    1650                1655                1660

Gly Val Leu Ala Ala Leu Ala Ala Tyr Cys Leu Ser Thr Gly Cys Val
1665                1670                1675                1680

Val Ile Val Gly Arg Val Val Leu Ser Gly Lys Pro Ala Ile Ile Pro
                1685                1690                1695

Asp Arg Glu Val Leu Tyr Arg Glu Phe Asp Glu Met Glu Glu Cys Ser
            1700                1705                1710

Gln His Leu Pro Tyr Ile Glu Gln Gly Met Met Leu Ala Glu Gln Phe
        1715                1720                1725

Lys Gln Lys Ala Leu Gly Leu Leu Gln Thr Ala Ser Arg Gln Ala Glu
    1730                1735                1740

Val Ile Ala Pro Ala Val Gln Thr Asn Trp Gln Lys Leu Glu Thr Phe
1745                1750                1755                1760

Trp Ala Lys His Met Trp Asn Phe Ile Ser Gly Ile Gln Tyr Leu Ala
                1765                1770                1775

```
Gly Leu Ser Thr Leu Pro Gly Asn Pro Ala Ile Ala Ser Leu Met Ala
            1780                1785                1790

Phe Thr Ala Ala Val Thr Ser Pro Leu Thr Thr Ser Gln Thr Leu Leu
            1795                1800                1805

Phe Asn Ile Leu Gly Gly Trp Val Ala Ala Gln Leu Ala Ala Pro Gly
            1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Ile Asp Ile Leu Ala Gly Tyr Gly
                1845                1850                1855

Ala Gly Val Ala Gly Ala Leu Val Ala Phe Lys Ile Met Ser Gly Glu
                1860                1865                1870

Val Pro Ser Thr Xaa Asp Leu Val Asn Leu Leu Pro Ala Ile Leu Ser
            1875                1880                1885

Pro Gly Ala Leu Val Val Gly Val Val Cys Ala Ala Ile Leu Arg Arg
            1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935

Glu Ser Asp Ala Ala Ala Arg Val Thr Ala Ile Xaa Xaa Ser Leu Thr
                1940                1945                1950

Val Thr Gln Leu Leu Arg Arg Leu His Gln Trp Ile Ser Ser Glu Cys
                1955                1960                1965

Thr Thr Pro Cys Ser Gly Ser Trp Leu Arg Asp Ile Trp Asp Trp Ile
            1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Lys
                2005                2010                2015

Gly Val Trp Arg Xaa Asp Gly Ile Met His Thr Arg Cys His Cys Gly
                2020                2025                2030

Ala Glu Ile Thr Gly His Val Lys Asn Gly Thr Met Arg Ile Val Gly
            2035                2040                2045

Pro Arg Thr Cys Arg Asn Met Trp Ser Gly Thr Phe Pro Ile Asn Ala
2050                2055                2060

Tyr Thr Thr Gly Pro Cys Thr Pro Leu Pro Ala Pro Asn Tyr Thr Phe
2065                2070                2075                2080

Ala Leu Trp Arg Val Ser Ala Glu Glu Tyr Val Glu Ile Arg Gln Val
            2085                2090                2095

Gly Asp Phe His Tyr Val Thr Gly Met Thr Thr Asp Asn Leu Lys Cys
            2100                2105                2110

Pro Cys Gln Val Pro Ser Pro Glu Phe Phe Thr Glu Leu Asp Gly Val
            2115                2120                2125

Arg Leu His Arg Phe Ala Pro Pro Cys Lys Pro Leu Leu Arg Glu Glu
            2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
            2165                2170                2175

Asp Pro Ser His Ile Thr Ala Glu Ala Ala Gly Arg Arg Leu Ala Arg
            2180                2185                2190
```

```
Gly Ser Pro Pro Ser Val Ala Ser Ser Ala Ser Gln Leu Ser Ala
        2195                2200                2205

Pro Ser Leu Lys Ala Thr Cys Thr Ala Asn His Asp Ser Pro Asp Ala
    2210                2215                2220

Glu Leu Ile Glu Ala Asn Leu Leu Trp Arg Gln Met Gly Gly Asn
2225                2230                2235                2240

Ile Thr Arg Val Glu Ser Glu Asn Lys Val Val Ile Leu Asp Ser Phe
                2245                2250                2255

Asp Pro Leu Val Ala Glu Asp Glu Arg Glu Ile Ser Val Pro Ala
            2260                2265                2270

Glu Ile Leu Arg Lys Ser Arg Arg Phe Ala Gln Ala Leu Pro Val Trp
            2275                2280                2285

Ala Arg Pro Asp Tyr Asn Pro Pro Leu Val Glu Thr Trp Lys Lys Pro
    2290                2295                2300

Asp Tyr Glu Pro Pro Val Val His Gly Cys Pro Leu Pro Pro Lys
2305                2310                2315                2320

Ser Pro Pro Val Pro Pro Pro Arg Lys Lys Arg Thr Val Val Leu Thr
                2325                2330                2335

Glu Ser Thr Leu Ser Thr Ala Leu Ala Glu Leu Ala Xaa Arg Ser Phe
                2340                2345                2350

Gly Ser Ser Ser Thr Ser Gly Ile Thr Gly Asp Asn Thr Thr Thr Ser
        2355                2360                2365

Ser Glu Pro Ala Pro Ser Gly Cys Pro Pro Asp Ser Asp Ala Glu Ser
    2370                2375                2380

Xaa Xaa Ser Met Pro Pro Leu Glu Gly Glu Pro Gly Asp Pro Asp Leu
2385                2390                2395                2400

Ser Asp Gly Ser Trp Ser Thr Val Ser Ser Glu Ala Asn Ala Glu Asp
            2405                2410                2415

Val Val Cys Cys Ser Met Ser Tyr Ser Trp Thr Gly Ala Leu Val Thr
            2420                2425                2430

Pro Cys Ala Ala Glu Glu Gln Lys Leu Pro Ile Asn Ala Leu Ser Asn
        2435                2440                2445

Ser Leu Leu Arg His His Asn Leu Val Tyr Ser Thr Thr Ser Arg Ser
    2450                2455                2460

Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
                2485                2490                2495

Lys Val Lys Ala Asn Xaa Leu Ser Val Glu Glu Ala Cys Ser Leu Thr
            2500                2505                2510

Pro Pro His Ser Ala Lys Ser Lys Phe Gly Tyr Gly Ala Lys Asp Val
        2515                2520                2525

Arg Cys His Ala Arg Lys Ala Val Thr His Ile Asn Ser Val Trp Lys
        2530                2535                2540

Asp Leu Leu Glu Asp Asn Val Thr Pro Ile Asp Thr Thr Ile Met Ala
2545                2550                2555                2560

Lys Asn Glu Val Phe Cys Val Gln Pro Glu Lys Gly Gly Arg Lys Pro
                2565                2570                2575

Ala Arg Leu Ile Val Phe Pro Asp Leu Gly Val Arg Val Cys Glu Lys
            2580                2585                2590

Met Ala Leu Tyr Asp Val Val Thr Lys Leu Pro Leu Ala Val Met Gly
            2595                2600                2605
```

```
Ser Ser Tyr Gly Phe Gln Tyr Ser Pro Gly Gln Arg Val Glu Phe Leu
    2610                2615                2620

Val Gln Ala Trp Lys Ser Lys Lys Thr Pro Met Gly Phe Ser Tyr Asp
2625                2630                2635                2640

Thr Arg Cys Phe Asp Ser Thr Val Thr Glu Ser Asp Ile Arg Thr Glu
                2645                2650                2655

Glu Ala Ile Tyr Gln Cys Cys Asp Leu Asp Pro Gln Ala Arg Val Ala
                2660                2665                2670

Ile Lys Ser Leu Thr Glu Arg Leu Tyr Val Gly Gly Pro Leu Thr Asn
            2675                2680                2685

Ser Xaa Gly Glu Asn Cys Gly Tyr Arg Arg Cys Arg Ala Ser Gly Val
        2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
                2725                2730                2735

Gly Asp Asp Leu Val Val Ile Cys Glu Ser Ala Gly Val Gln Glu Asp
                2740                2745                2750

Ala Ala Ser Leu Arg Ala Phe Thr Glu Ala Met Thr Arg Tyr Ser Ala
            2755                2760                2765

Pro Pro Gly Asp Pro Pro Gln Pro Glu Tyr Asp Leu Glu Leu Ile Thr
        2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
                2805                2810                2815

Trp Glu Thr Ala Arg His Thr Pro Val Asn Ser Trp Leu Gly Asn Ile
                2820                2825                2830

Ile Met Phe Ala Pro Thr Leu Trp Ala Arg Met Ile Leu Met Thr His
            2835                2840                2845

Phe Phe Ser Val Leu Ile Ala Arg Asp Gln Leu Glu Gln Ala Leu Asp
    2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
                2885                2890                2895

Tyr Ser Pro Gly Glu Ile Asn Arg Val Ala Ala Cys Leu Arg Lys Leu
            2900                2905                2910

Gly Val Pro Pro Leu Arg Ala Trp Xaa His Arg Ala Arg Ser Val Arg
            2915                2920                2925

Ala Arg Leu Leu Ala Arg Gly Gly Arg Ala Ala Ile Cys Gly Lys Tyr
    2930                2935                2940

Leu Phe Asn Trp Ala Val Arg Thr Lys Leu Lys
2945                2950                2955
```